(12) United States Patent
Sterrett et al.

(10) Patent No.: US 11,744,596 B2
(45) Date of Patent: *Sep. 5, 2023

(54) RETROGRADE CUTTING INSTRUMENT

(71) Applicant: Arthrex, Inc., Naples, FL (US)

(72) Inventors: Jerry Sterrett, Naples, FL (US); David C. Koogle, Jr., Bonita Springs, FL (US); Ronald C. Iannarone, Aiken, SC (US); Ricardo Albertorio, Naples, FL (US)

(73) Assignee: Arthrex, Inc., Naples, FL (US)

( * ) Notice: Subject to any disclaimer, the term of this patent is extended or adjusted under 35 U.S.C. 154(b) by 134 days.

This patent is subject to a terminal disclaimer.

(21) Appl. No.: 17/391,774

(22) Filed: Aug. 2, 2021

(65) Prior Publication Data

US 2021/0353305 A1 Nov. 18, 2021

Related U.S. Application Data

(60) Continuation of application No. 15/349,128, filed on Nov. 11, 2016, now Pat. No. 11,202,639, which is a continuation of application No. 14/516,084, filed on Oct. 16, 2014, now Pat. No. 9,526,510, which is a division of application No. 12/397,263, filed on Mar.
(Continued)

(51) Int. Cl.
*A61B 17/16* (2006.01)
*A61B 17/32* (2006.01)
*A61B 1/317* (2006.01)
*A61B 90/00* (2016.01)
(Continued)

(52) U.S. Cl.
CPC .......... *A61B 17/1617* (2013.01); *A61B 1/317* (2013.01); *A61B 17/1635* (2013.01); *A61B 17/1662* (2013.01); *A61B 17/1675* (2013.01); *A61B 17/32002* (2013.01); *A61B 17/3472* (2013.01); *A61B 90/06* (2016.02); *A61B 2017/2927* (2013.01); *A61B 2090/062* (2016.02)

(58) Field of Classification Search
CPC ............ A61B 17/1662; A61B 17/1617; A61B 17/1675
See application file for complete search history.

(56) References Cited

U.S. PATENT DOCUMENTS 5,147,373 A 9/1992 Ferzli
5,429,504 A 7/1995 Peltier et al.
(Continued)

FOREIGN PATENT DOCUMENTS

| EP | 1 690 499 A2 | 8/2006 |
| WO | WO-98/49945 A1 | 11/1998 |
| WO | WO-2007/047065 A1 | 4/2007 |

OTHER PUBLICATIONS

Opposition Decision for EP Patent No. 2098177, May 24, 2016.
(Continued)

*Primary Examiner* — Samuel S Hanna
(74) *Attorney, Agent, or Firm* — Blank Rome LLP

(57) ABSTRACT

A retrograde cutting instrument and method of retrograde drilling using such an instrument. A method of forming a socket includes providing a retrograde cutter, inserting the cutter into a joint with a blade of the cutter in a straight position, pivoting the blade to a non-straight flip position, locking the blade in the flip position, and retrograde drilling a socket using the blade in the flip position.

4 Claims, 6 Drawing Sheets

Related U.S. Application Data 3, 2009, now Pat. No. 8,888,781, which is a continuation-in-part of application No. 12/114,599, filed on May 2, 2008, now Pat. No. 8,652,139.

(60) Provisional application No. 61/033,252, filed on Mar. 3, 2008, provisional application No. 60/915,607, filed on May 2, 2007.

(51) Int. Cl.
*A61B 17/34* (2006.01)
*A61B 17/29* (2006.01)

(56) References Cited

U.S. PATENT DOCUMENTS

| | | | |
|---|---|---|---|
| 5,431,671 | A | 7/1995 | Nallakrishnan |
| 5,649,947 | A | 7/1997 | Auerbach et al. |
| 5,928,239 | A | 7/1999 | Mirza |
| 5,941,706 | A | 8/1999 | Ura |
| 6,235,057 | B1 | 5/2001 | Roger et al. |
| 6,679,886 | B2 | 1/2004 | Weikel |
| 6,884,246 | B1 | 4/2005 | Sonnabend et al. |
| RE42,757 | E | 9/2011 | Kuslich |
| 2001/0034526 | A1 | 10/2001 | Kuslich |
| 2002/0032447 | A1 | 3/2002 | Weikel et al. |
| 2002/0183758 | A1 | 12/2002 | Middleton |
| 2003/0135218 | A1 | 7/2003 | Eckman |
| 2004/0092936 | A1 | 5/2004 | Miller et al. |
| 2004/0092988 | A1* | 5/2004 | Shaolian ............ A61B 17/1675 606/167 |
| 2004/0199166 | A1 | 10/2004 | Schmieding et al. |
| 2004/0210231 | A1 | 10/2004 | Boucher et al. |
| 2005/0240193 | A1 | 10/2005 | Layne et al. |
| 2005/0261684 | A1 | 11/2005 | Shaolian et al. |
| 2006/0195112 | A1 | 8/2006 | Ek |
| 2007/0233138 | A1 | 10/2007 | Figueroa et al. |
| 2007/0239159 | A1* | 10/2007 | Altarac ............ A61B 17/7091 606/86 A |
| 2007/0250067 | A1 | 10/2007 | Schmieding et al. |
| 2007/0276391 | A1 | 11/2007 | Graves et al. |
| 2008/0039852 | A1 | 2/2008 | Schmieding et al. |
| 2008/0114364 | A1* | 5/2008 | Goldin ........... A61B 17/320016 606/170 |
| 2008/0172125 | A1 | 7/2008 | Ek |
| 2008/0249481 | A1 | 10/2008 | Crainich et al. |
| 2008/0275512 | A1 | 11/2008 | Albertorio et al. |
| 2008/0306483 | A1 | 12/2008 | Iannarone |
| 2010/0076503 | A1 | 3/2010 | Beyar |
| 2010/0268237 | A1 | 10/2010 | Carl et al. |

OTHER PUBLICATIONS

Opposition Decision, EP Patent No. 1987786, Apr. 4, 2016.
EP Extended Search Report, EP Patent No. 2218411, dated Jul. 1, 2010.
Notice of Opposition, EP Application No. 2218411, Jul. 24, 2012.
Arthrex "ACL Reconstruction with FlipCutter", Screenshots showing availability of video, on Jan. 1, 2009.
Arthrex newsletter *Scope This Out* "A Technical Pearls Newsletter for Arthroscopists" Winter 2008-2009, vol. 10, No. 4, pp. 1-8.
Arthrex newsletter *Scope This Out* "A Technical Pearls Newsletter for Arthroscopists" Summer 2009, vol. 11, No. 4, pp. 1-8.
Arthrex "Flipcutter", Screenshots showing availability date of Arthrex newsletters on Jul. 1, 2009 and Jan. 1, 2009 relating to Flipcutter.
Opposition filed by Smith & Nephew against corresponding EP 2098177 B1, dated Jul. 15, 2014.
Grounds for Appeal filed against Decision upholding EP Patent No. 1987786, dated Aug. 11, 2016.

* cited by examiner

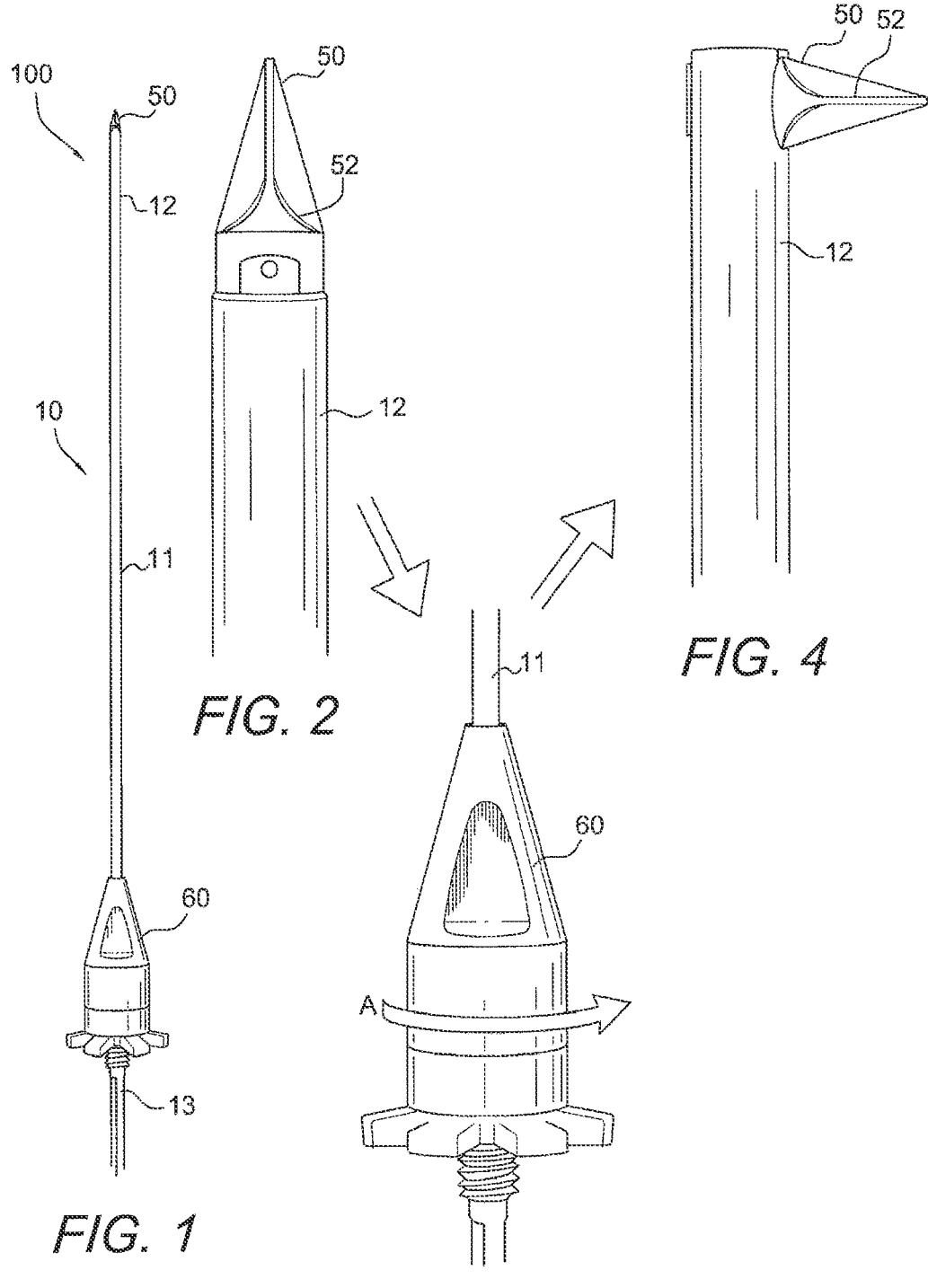

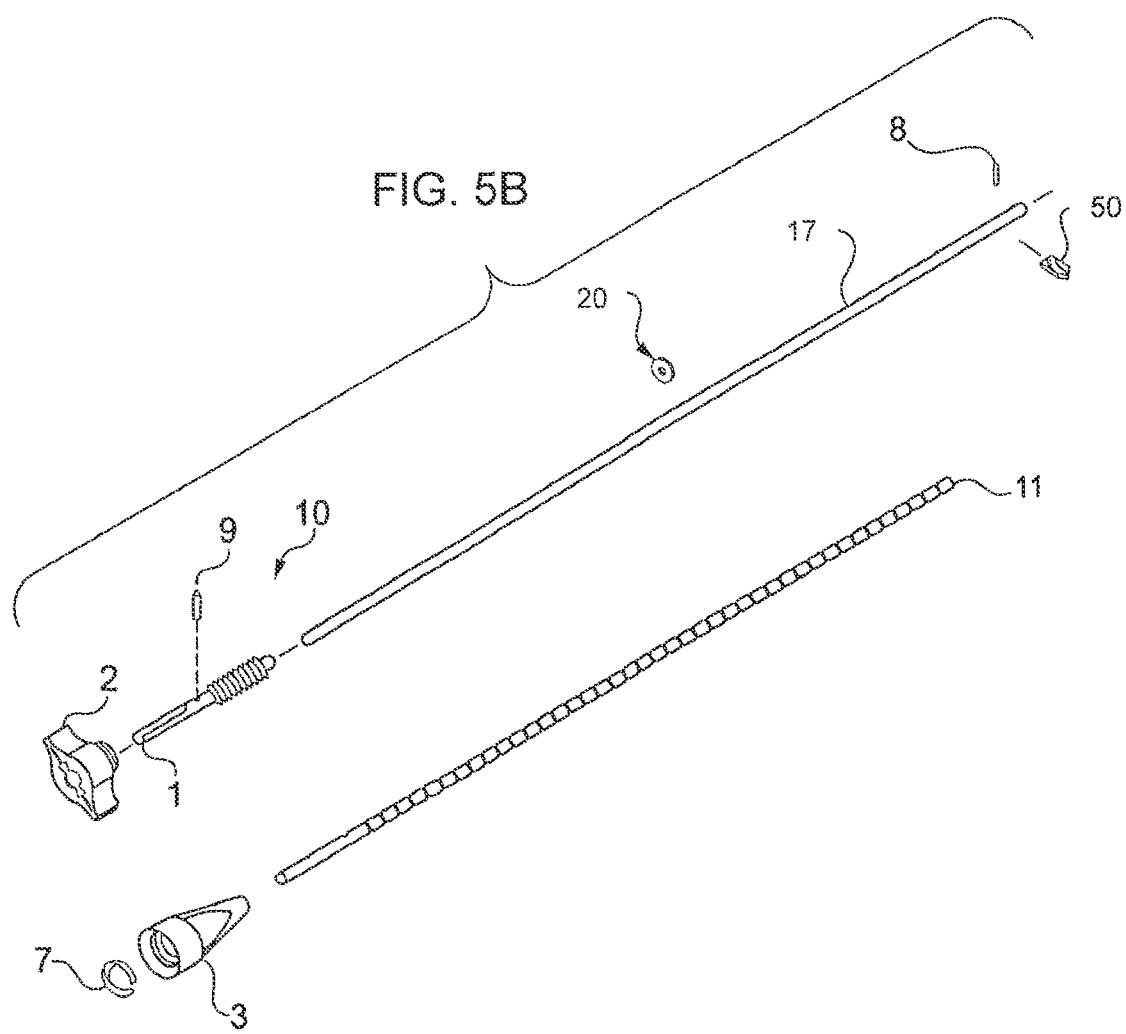

RETROGRADE CUTTING INSTRUMENT

CROSS-REFERENCE TO RELATED APPLICATIONS

This is a continuation of U.S. application Ser. No. 15/349,128, filed Nov. 11, 2016, which is continuation of U.S. application Ser. No. 14/516,084, filed Oct. 16, 2014, now U.S. Pat. No. 9,526,510, which is a divisional of U.S. application Ser. No. 12/397,263, filed Mar. 3, 2009, now U.S. Pat. No. 8,888,781, which claims the benefit of U.S. Provisional Application No. 61/033,252, filed Mar. 3, 2008, and which is a continuation-in-part of U.S. application Ser. No. 12/114,599, filed May 2, 2008, now U.S. Pat. No. 8,652,139, which in turn claims the benefit of U.S. Provisional Application No. 60/915,607, filed May 2, 2007, the entire disclosures of which are incorporated by reference herein.

FIELD OF THE INVENTION

The present invention relates to arthroscopic surgical methods and instruments and, more specifically, to an instrument and method of retrograde repair and reconstruction.

BACKGROUND OF THE INVENTION

During arthroscopic surgery, a small incision is made in the skin covering the arthroscopic site or joint, and a cannula is inserted in the incision to provide a pathway for surgical instruments to be placed in the joint and manipulated through arthroscopic visualization. Surgical instruments inserted through cannulas must be long and thing this presents limitations on instruments for cutting tissue, as the diameter of the cannula ordinarily limits the width of the cutting implement.

Retrograde drilling of sockets and tunnels for ACL reconstruction is known and described, for example, in U.S. Pat. No. 8,668,738, entitled "Method and Apparatus for ACL Reconstruction using Retrograde Cutter." In such a method, sockets in bone created by retrograde cutting. A rotary cutter, mounted onto an insertion post of a guide, is inserted through an anteromedial portal into the knee joint. A drill pin is drilled through the tibia and advanced until it contacts and engages a cannulation in the rotary cutter on the guide. Further rotation of the drill pin disengages the rotary cutter from the guide. The retrograde drill pin is then retracted and simultaneously rotated for retrograde cutting of a socket or tunnel of desired depth in the tibia. A similar method can be used for drilling a femoral socket or tunnel. A need exists for a surgical cutting instrument that can be used arthroscopically for retrograde drilling of tunnels or sockets in bone without requiring a rotary cutter and drill pin. As with all arthroscopic instruments, the surgical cutting instrument must be configured for insertion through a narrow cannula, but able to cut a relatively wide tunnel or socket.

A need also exists for a surgical cutter that is stable during knee arthroscopy and that provides drilling of femoral and tibial sockets or tunnels independently of one another and minimizes incisions of distal cortices and reduces intraarticular bone fragmentation of tunnel rims.

Accordingly, a need exists for a surgical drilling/cutting instrument that is configured to allow improved handling of the instrument within a joint capsule, for example the knee capsule, during ACL reconstruction. A need also exists for a surgical cutter that is stable during knee arthroscopy during the cutting mode, and that also provides drilling of femoral and tibial sockets or tunnels.

SUMMARY OF THE INVENTION

The present invention provides a retrograde cutter having a cutting tip pivotably coupled to the distal end of the shaft. The cutting tip is capable of movement from a first position, which is generally aligned with the longitudinal axis of the shaft, to a second position, which is not aligned with the longitudinal axis, the cutting tip extending beyond the distal end of the shaft when the cutting tip is in the first position.

The cutting tip is configured such that, when the cutting tip is in an articular joint space of the articular joint, the cutting tip is pivotable from the first position to the second position for retrograde drilling of the bone socket when the shaft of the retrograde cutting instrument is rotated and the retrograde cutting instrument is pulled proximally, such that the bone socket faces the articular joint space.

The present invention provides a flip retrograde cutter that creates a recipient site socket from the inside out, i.e., using a retrograde technique, with minimal incisions of distal cortices and reduced intraarticular bone fragmentation of tunnel rims.

These and other features and advantages of the invention will be more apparent from the following detailed description that is provided in connection with the accompanying drawings and illustrate exemplary embodiments of the invention.

BRIEF DESCRIPTION OF THE DRAWINGS

FIG. 1 illustrates a side view of the combined flip cutter and drill of the present invention;

FIG. 2 illustrates an enlarged view of the combined flip cutter and drill of FIG. 1, with the drill end in the "straight" (or drilling mode) configuration;

FIG. 3 illustrates an enlarged view of the actuating mechanism of the combined flip cutter and drill of FIG. 1;

FIG. 4 illustrates an enlarged view of the combined flip cutter and drill of FIG. 1, with the drill end in the "flip" (or cutting mode) configuration;

FIGS. 5A and 5B illustrate another perspective view and an exploded view, respectively, of the combined flip cutter and drill of the present invention;

DETAILED DESCRIPTION OF THE PREFERRED EMBODIMENTS

Figure 5A:
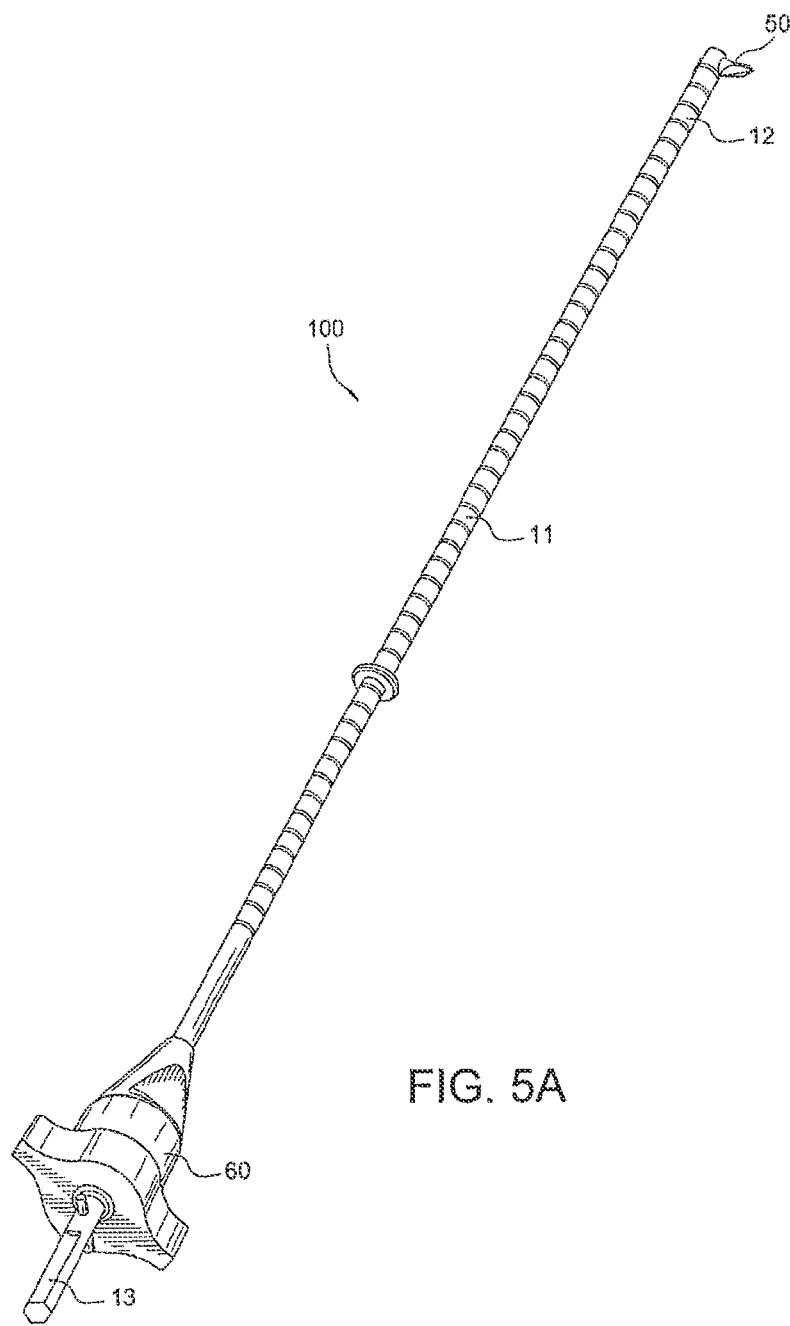

The following description is provided to enable any person skilled in the art to make and use the invention and sets forth the best modes contemplated by the inventors of carrying out their invention. Various modifications, however, will remain readily apparent to those skilled in the art.

The present invention provides a combined flip cutter and drill instrument that is designed to function in either a drilling mode or a cutting mode. The flip cutter and drill of the present invention is provided with a drill which has a conical, multi-blade configuration and which engages the shaft of the instrument to articulate between at least a first "straight" position (for example, about parallel to the longitudinal axis of the instrument) and at least a second "flip" position (for example, a non-parallel position relative to the longitudinal axis of the instrument).

The flip cutter and drill of the present invention may be employed in a regular manner (when in the drilling mode or "straight" position, for example), or in a retrograde manner (when in the cutting mode or "flip" position for example) to form a recipient socket (to accommodate an osteochondral transplant, or to allow retrograde fixation of a graft within two sockets, for example).

Referring now to the drawings, where like elements are designated by like reference numerals, FIGS. 1-8 illustrate various components of a combined flip cutter and drill 100 of the present invention. The flip cutter and drill 100 of the present invention is similar to the flip retrograde cutting instrument 100 of U.S. Pat. No. 8,652,139 (the disclosure of which is incorporated in its entirety herewith) but differs in that blade 5 of the flip retrograde cutter 100 is replaced by a drill or cutter 50 which is conical with a plurality of edges 52 (FIGS. 2 and 4) and/or has a plurality of blades with sharp cutting edges 52 (FIGS. 6-8), as described in more detail below, to allow drilling both in a regular manner (in an antegrade manner) and in a retrograde manner.

The flip cutter and drill 100 includes a cannulated elongated body 10 having a distal end 12 and a proximal end 13, as shown in FIGS. 1, 5A and 5B. The body 10 of the flip cutter and drill 100 includes a cannulated shaft or outer tube 11 provided at its distal end 12. The outer tube 11 houses an inner tube or inner member 17 (as shown in more detail in FIG. 8, for example) provided with a drill 50 having a plurality of cutting edges 52 (as shown in FIG. 2, for example). Details of specific exemplary embodiments of the drill 50 of the flip cutter and drill 100 are illustrated in FIGS. 2, 4 and 6-8; however, the invention contemplates other shapes and geometries for the drill 50.

Figure 6:
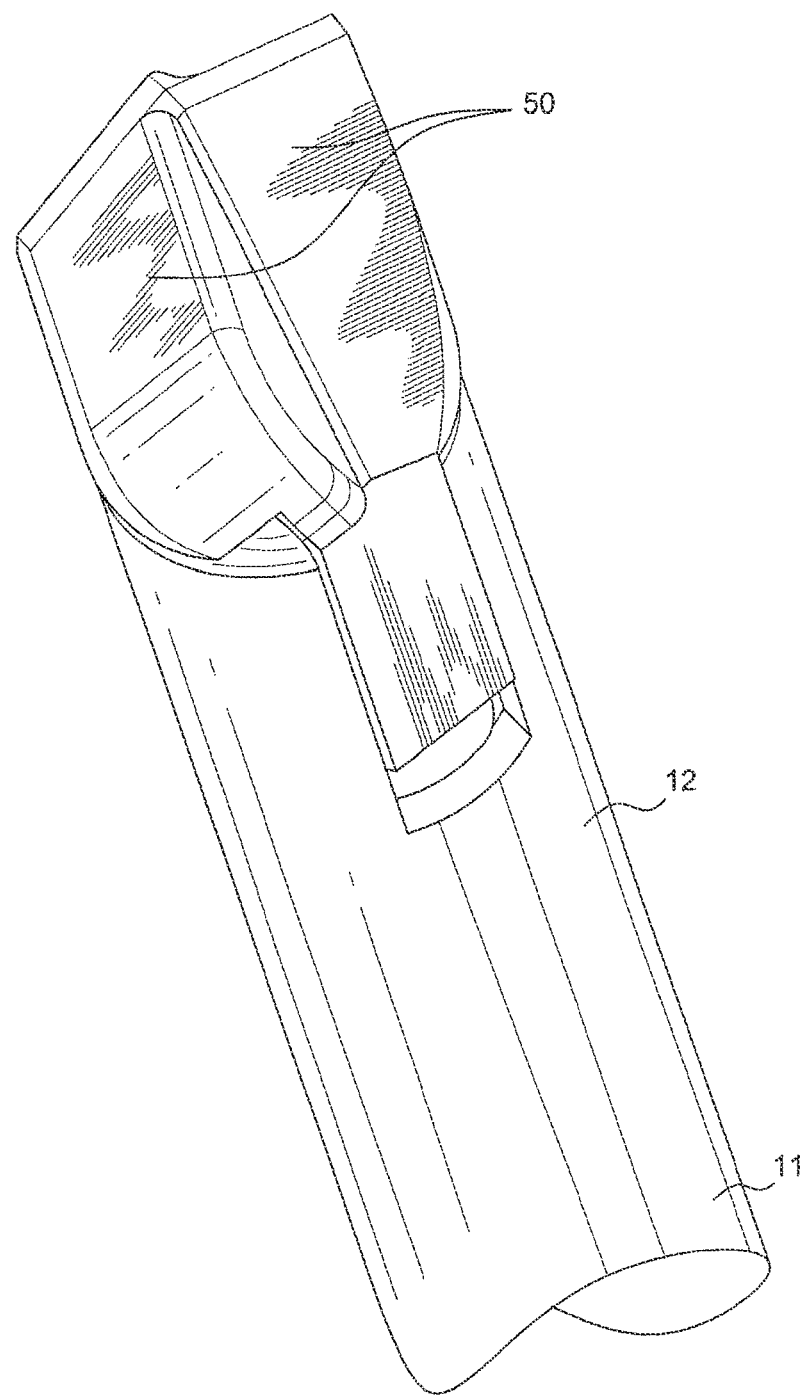
FIG. 6 illustrates an enlarged view of the distal end of the combined flip cutter and drill of FIG. 1, with the drill end in the "straight" (or drilling mode) configuration.

Drill 50 illustrated in detail in FIGS. 2, 4 and 6-8 is configured to engage the shaft or inner tube 17 of the instrument 100 and to articulate between at least first and second positions. In an exemplary embodiment, drill 50 engages inner tube 17 in a first or "straight" position (for example, about parallel to the longitudinal axis of the cutting instrument 100), as shown in FIGS. 1, 2 and 6. In the "straight" configuration, instrument 100 functions in the antegrade drilling mode.

Figure 7:
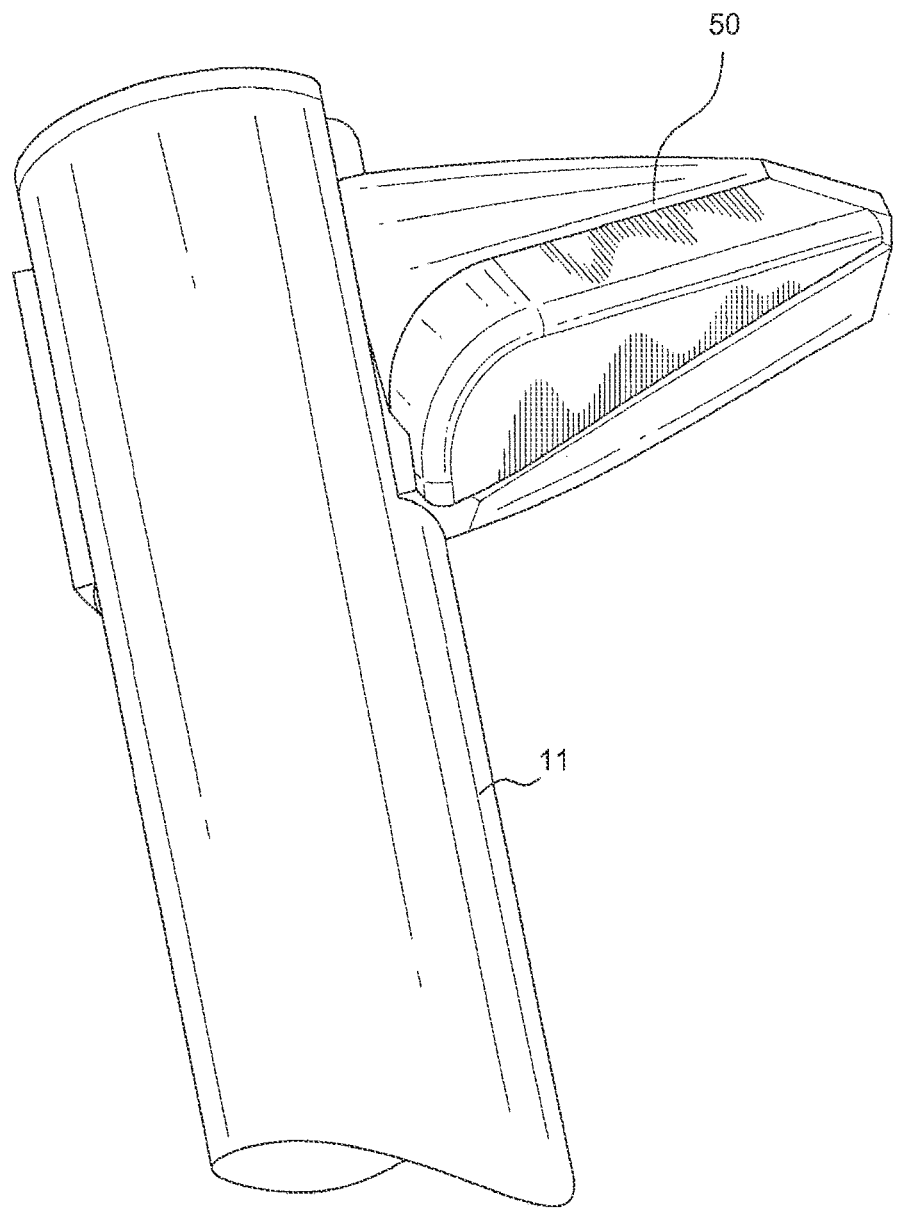
FIG. 7 illustrates an enlarged view of the distal end of the combined flip cutter and drill of FIG. 1, with the drill end in the "flip" (or cutting mode) configuration.
Figure 8:
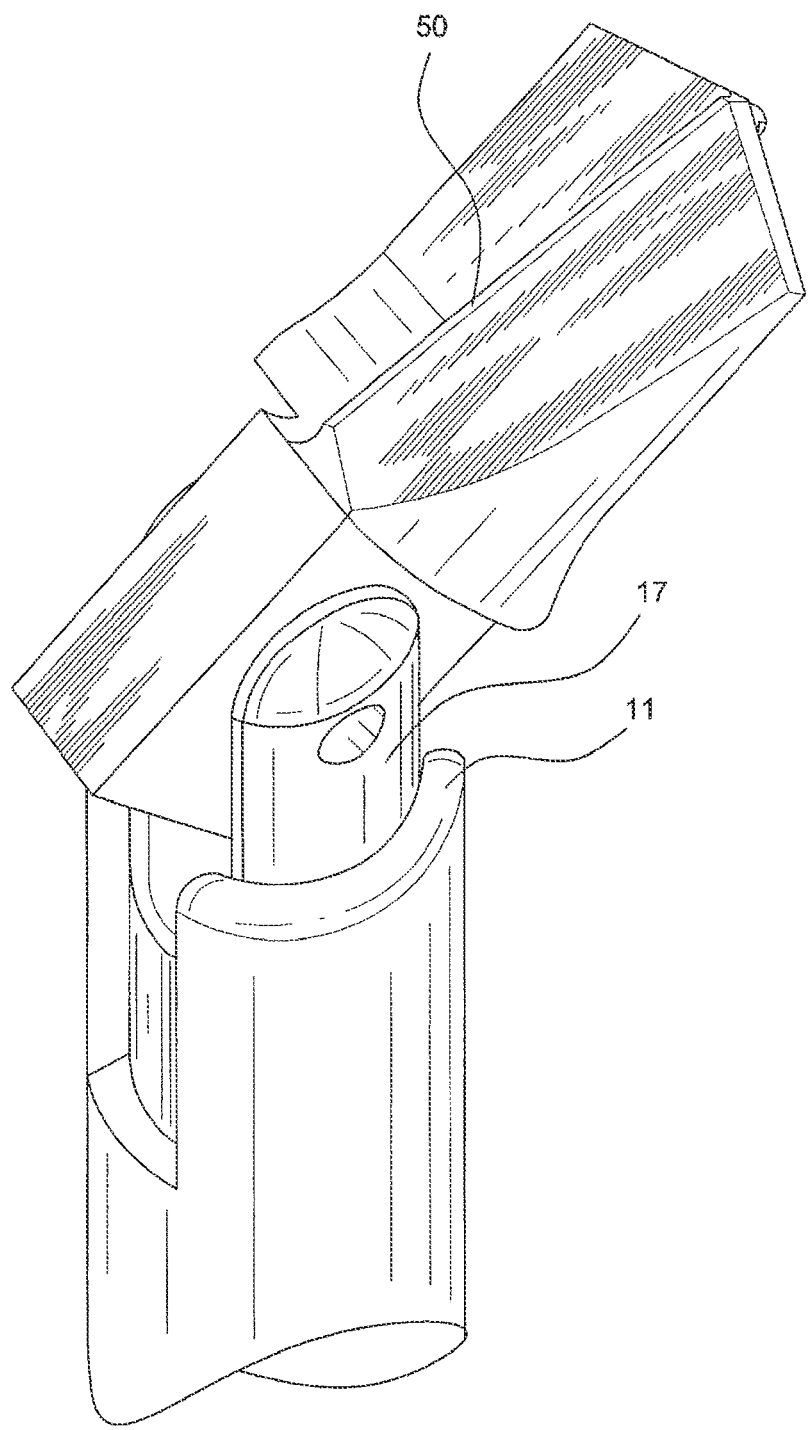
FIG. 8 illustrates an enlarged view of the distal end of the combined flip cutter and drill of FIG. 1, with the outer tube in a retracted position to show the pivoting axis.

In an exemplary embodiment, drill 50 engages the shaft of the instrument in a second or "flip" position (for example, a non-parallel position relative to the longitudinal axis of the cutting instrument 100), as shown in FIGS. 4, 5A, 5B and 7. In the "flip" configuration, instrument 100 functions in the cutting mode (for example, retrograde cutting). The non-parallel position shown in FIGS. 4, 5 and 7 is about perpendicular to the longitudinal axis of the cutting instrument 100; however, the present invention contemplates embodiments wherein drill 50 forms any angle with the shaft (for example, an angle between about 10 to about 170 degrees relative to the longitudinal axis of the cutting instrument 100, as shown in FIG. 8, for example).

In use, once the drilling/cutting instrument 100 is inserted into a joint, for example, a knee joint, the surgeon rotates (in the direction of arrow "A" of FIG. 3) actuating mechanism 60 to pivot the cutting drill 50 into the "flip" configuration (i.e., into a position other than the "straight" position), wherein the cutting tip is disposed at an angle of about 90 degrees with respect to the shaft of the instrument. The surgeon may also gradually increase or decrease the angle, as desired and in accordance with the characteristics of the surgical site. Once the drill is articulated in the desired "flip" position, the drill is preferably locked in position by tightening the tube 11. A drilling operation (when the instrument is in the "straight" position) or a retrograde cutting operation (when the instrument is in the "flip" position) may be subsequently carried, as desired and as known in the art.

As seen in FIGS. 5A and 5B, actuating mechanism 60 comprises a driver end 1, a nut 2, a hub 3, a retainer ring 7, two pins (a slotted spring pin 9 and a pin 10), and the shaft 11. The flip cutter and drill 100 is preferably assembled by first pressing the shaft 11 into the hub 3 until the shaft 11 bottoms out. The retainer ring 7 is then inserted into a groove of the hub 3 to form a first sub-assembly. Next, the inner member 17 is inserted into an end of the driver end 1 and securely engaged using the pin 10. The first sub-assembly, described above, is slid over the assembled inner member 17 and driver end 1. Next, the drill 50 is slid into slot of the inner member 17 and securely engaged using cross pin 8. The nut 2 is then screwed onto the other end of the driver end 1. Next, the hub 3 is pulled back while advancing the nut 2 until the retainer ring 7 engages and the slotted spring pin 9 is inserted into a through hole in the driver end 1 to secure the driver end 1 against the nut 2. An O-Ring 20 may be slid over the shaft 11, having laser etches on its circumference. The O-Ring 20 may be used to measure depth during retrograde drilling.

The present invention may be used to form various sockets or tunnels to allow fixation of a graft (for example, a semitendonosus allograft) or to allow replacement of osteochondral cores or implants in a retrograde manner, to obviate inserting harvesters into the joint. For example, drilling/cutting instrument 100 of the present invention may be employed for the formation of sockets during an "all-inside ACL RetroConstruction™" for ligament repair, which may comprise, for example, the steps of: (i) drilling at least a femoral and tibial tunnel or socket using a retrograde drill technique employing the drilling/cutting instrument 100 of FIGS. 1-8; (ii) providing a graft (soft tissue graft or BTB graft) in the vicinity of the sockets; and (iii) securing the graft within the femoral and tibial tunnels (sockets).

According to yet another embodiment, an exemplary method of ACL RetroConstruction™ of the present invention comprises, for example, the steps of: (i) drilling a femoral socket; (ii) drilling a tibial tunnel or socket using a retrograde drill technique employing the drilling/cutting instrument 100 of FIGS. 1-8; (iii) providing a graft (soft tissue graft or BTB graft) in the vicinity of the sockets; (iv) securing the graft (soft tissue graft or BTB graft) to a continuous loop/button construct comprising a button with an oblong configuration and provided with an inside eyelet that allows the passage of the continuous loop, preferably a suture loop; (v) passing the graft with the button through the femoral tunnel; (vi) securing the button to the femoral cortex once the button exits the femoral socket; and (vii) securing the graft in the tibial tunnel or socket.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. It is preferred, therefore, that the present invention be limited not by the specific disclosure herein, but only by the appended claims.

What is claimed is:

1. A combined antegrade and retrograde surgical drilling instrument, comprising:
- a cannulated shaft extending from a distal end to a proximal end along a longitudinal axis, the distal end having a slot extending through the cannulated shaft;
- an inner member received in the cannulated shaft and longitudinally movable with respect to the cannulated shaft; and
- a pivotable drilling member pivotably connected to the inner member and having a configuration for drilling a socket or tunnel through bone and having a plurality of cutting edges, the drilling member being pivotable, by longitudinal movement of the inner member relative to the cannulated shaft, between a first position in which the drilling member is axially aligned with the longitudinal axis of the cannulated shaft for antegrade drilling, and a second position in which the drilling member is at about a 90 degree angle with respect to the longitudinal axis of the cannulated shaft for retrograde drilling, and when the drilling member is in the second position, the plurality of cutting edges extend outside of the slot at the distal end of the cannulated shaft,
- wherein the drilling member is configured for the antegrade drilling when the drilling member is in the first position, and
- wherein the drilling member is configured for the retrograde drilling when the drilling member is in the second position.

2. The surgical instrument of claim 1, wherein the slot extends diametrically through the distal end of the cannulated shaft and defines distal opposing shoulders in the cannulated shaft, and the drilling member is seated between the opposing shoulders when the drilling member is in the second position.

3. The surgical instrument of claim 2, further comprising a hub attached to the proximal end of the cannulated shaft for actuating the drilling member from the first position to the second position by longitudinally moving the inner member with respect to the cannulated shaft.

4. A combined antegrade and retrograde surgical drilling instrument, comprising:
- a cannulated shaft extending from a distal end to a proximal end along a longitudinal axis, the distal end having a slot and an end face that is open;
- an inner member received in the cannulated shaft and longitudinally movable with respect to the cannulated shaft; and
- a drilling member having a configuration pivotably connected to the inner member and for drilling a socket or tunnel through bone, at least a portion of the drilling member being pivotally movable with respect to the distal end of the cannulated shaft by longitudinal movement of the inner member relative to the cannulated shaft, the distal end of the cannulated shaft and the drilling member forming a flip configuration of the surgical instrument when the drilling member is pivoted outwardly with respect to the cannulated shaft for the retrograde drilling and a straight configuration of the surgical instrument when the drilling member is not pivoted with respect to the cannulated shaft for the antegrade drilling,
- the drilling member having a plurality of cutting edges for the antegrade and retrograde drilling, the drilling member being pivotable to a flip position in which the drilling member is about perpendicular to the longitudinal axis of the cannulated shaft when the surgical instrument is in the flip configuration such that the plurality of cutting edges of the drilling member extend outside of the slot at the distal end of the cannulated shaft,
- wherein the drilling member is configured for the antegrade drilling when the drilling member is in the straight configuration, and
- wherein the drilling member is configured for the retrograde drilling when the drilling member is in the flip configuration.

* * * * *